US006193477B1

(12) United States Patent
Falk et al.

(10) Patent No.: US 6,193,477 B1
(45) Date of Patent: Feb. 27, 2001

(54) LOW POWER ELECTROMAGNETIC PUMP

(75) Inventors: Theodore J. Falk, Clarence; W. Richard Brown, Clarence Center; Lawrence E. Morris, Bowmansville; Norbert W. Frenz, Jr., Clarence; Douglas K. Gillies, East Aurora; Raymond S. Konopa, Alden, all of NY (US)

(73) Assignee: Wilson Greatbatch Ltd., Clarence, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/342,372

(22) Filed: Jun. 29, 1999

Related U.S. Application Data

(60) Continuation of application No. 09/135,760, filed on Aug. 18, 1998, now Pat. No. 5,915,929, which is a division of application No. 08/804,948, filed on Feb. 24, 1997, now Pat. No. 5,797,733, which is a continuation of application No. 08/212,555, filed on Aug. 11, 1994, now abandoned.

(51) Int. Cl.[7] ............................. F04B 17/04; F04B 35/04
(52) U.S. Cl. ........................................... 417/415; 417/417
(58) Field of Search ..................... 417/415, 416, 417/417

(56) References Cited

U.S. PATENT DOCUMENTS 5,797,733 * 8/1998 Falk et al. ............................ 417/416
5,915,929 * 6/1999 Falk et al. ............................ 417/415

* cited by examiner

Primary Examiner—Teresa Walberg
Assistant Examiner—L Fastovsky
(74) Attorney, Agent, or Firm—Hodgson, Russ, Andrews, Woods & Goodyear LLP (57) ABSTRACT

All electromagnetic pump comprising a housing having fluid receiving and pumping chambers in communication with an inlet and outlet, respectively, an electromagnet carried by the housing external to the fluid chambers thereof, and an armature movable in the housing having a pole portion magnetically attracted by the electromagnet and a piston portion to force fluid out of the chambers and through the pump outlet. A path provides controlled bypass for bubbles in the fluid around the armature piston portion between the fluid pumping chamber and the fluid receiving chamber only during the return stroke of the armature.

Fluid inertial effect is reduced by an outlet orifice provided in the fluid path from the pump outlet and by a bypass orifice in the fluid bypass path, the outlet and bypass orifices being provided either individually or in combination depending upon the fluid flow characteristics of the system of which the pump is a part. An accumulator between the pump outlet and a catheter leading away from the pump alleviates inertial and viscous effects from the catheter. The armature pole portion has a fluid-contacting section of material which is compatible with and corrosion resistant to the fluid, and can be a body of magnetic material within a titanium enclosure or a body of chrome-molybdenum-iron alloy. The check valve and inlet are so arranged that the pump displacement can be reduced without reducing bubble pumping capability.

11 Claims, 4 Drawing Sheets

LOW POWER ELECTROMAGNETIC PUMP

This application is a continuation of Ser. No. 09/135,760, filed Aug. 18, 1998, U.S. Pat. No. 5,915,929, which is a Division of Ser. No. 08/804,948, filed Feb. 24, 1997, Now U.S. Pat. No. 5,797,133, which is a continuation of Ser. No. 08/212,555 filed Mar. 11, 1994, now abandoned.

BACKGROUND OF THE INVENTION

This invention relates to the art of electromagnetically operated fluid pumps, and more particularly to a new and improved electromagnetic pump which operates at extremely low power.

One area of use of the present invention is implantable drug delivery systems, although the principles of the present invention can be variously applied. The principal requirements for a pump in such applications are low power drain, since the pump must be driven by an implanted battery, and compatibility with the drug being pumped. Another important requirement is that the pump be capable of operating with bubbles present in the liquid being pumped. A related consideration is that the bubble pumping capability provided in the pump not give rise to inaccuracy caused by inertia of the fluid stream. Such inertial effect is a result of the momentum of the fluid stream being capable of maintaining motion of the stream for some time after completion of the pump piston stroke, and the fluid volume delivered as a result of the stroke is thereby increased. A further pump design consideration is providing a relatively small displacement pump which pumps bubbles in a manner equivalent to that of a larger displacement pump.

It would, therefore, be highly desirable to provide an electromagnetically operated pump which is safe, reliable, small in size, light in weight, which operates without excessive demand on the available energy supply, which is compatible with drugs or similar liquids to be pumped, which is capable of operating with bubbles present in the liquid being pumped, wherein the inertial effect on pump accuracy is reduced, and wherein the bubble pumping capability is not reduced by a reduction in pump displacement.

SUMMARY OF THE INVENTION

It is, therefore, a primary object of this invention to provide a new and improved electromagnetically operated pump.

It is a more particular object of this invention to provide such a pump which operates at extremely low power levels.

It is a further object of this invention to provide such a pump which is compatible with the fluid being pumped.

It is further object of this invention to provide such a pump which is electronically and magnetically efficient.

It is a further object of this invention to provide such a pump which is capable of operating with bubbles present in the fluid being pumped.

It is a further object of this invention to provide such a pump which reduces the fluid inertial effect on pump accuracy.

It is a more particular object of this invention to provide such a pump which is small in size, light in weight and efficient and reliable in operation.

It is a further object of this invention to provide such a pump wherein the displacement can be reduced without reducing the bubble pumping capability of the pump.

The present invention provides an electromagnetic pump comprising a housing having a fluid receiving chamber in communication with an inlet, a fluid pumping chamber in fluid communication with an outlet, check valve means operatively associated with the fluid receiving chamber for allowing fluid flow in a direction from the inlet toward the outlet and blocking fluid flow in a direction from the outlet to the inlet, electromagnet means carried by the housing located external to the fluid chambers thereof, and barrier means in the form of a thin diaphragm of fluid impermeable material which hermetically isolates the electromagnet from the fluid chambers. An armature movable in the housing has a pole portion located for magnetic attraction by the electromagnet means and has a piston portion to force fluid out of the chambers and through the pump outlet. The armature piston portion is movably supported in the pump housing and located on the inlet side of an armature plunger. The armature is moved from a rest position through a forward pumping stroke when attracted by the electromagnet means to force fluid from the receiving chamber through the outlet, and the armature is moved by biasing means in an opposite direction through a return stroke back to the rest position. There is also provided controlled means for providing a bypass path for bubbles and fluid around the armature piston portion between the fluid pumping chamber and the fluid receiving chamber only during the return stroke of the armature.

The fluid inertial effect is reduced by means for providing an orifice in the path of fluid flow from the pump outlet and by means in the bypass path for providing an orifice for fluid flow in that path, the outlet and bypass orifices being provided either individually or in combination depending upon the fluid flow characteristics of the system of which the pump is a part. An accumulator means in the fluid flow path between the pump outlet and a catheter leading away from the pump alleviates inertial and viscous effects arising from the catheter. The armature pole portion has a fluid-contacting section of material which is compatible with and corrosion resistant to the fluid, and in one aspect is a body of magnetic material within a titanium enclosure and in another aspect is a body of chrome-molybdenum-iron alloy. The check valve means and inlet are so arranged that the pump displacement can be reduced without reducing the bubble pumping capability of the pump.

The foregoing and additional advantages and characterizing features of the present invention will become clearly apparent upon a reading of the ensuing detailed description together with the included drawing wherein:

DETAILED DESCRIPTION OF THE ILLUSTRATED EMBODIMENTS

Figure 1:
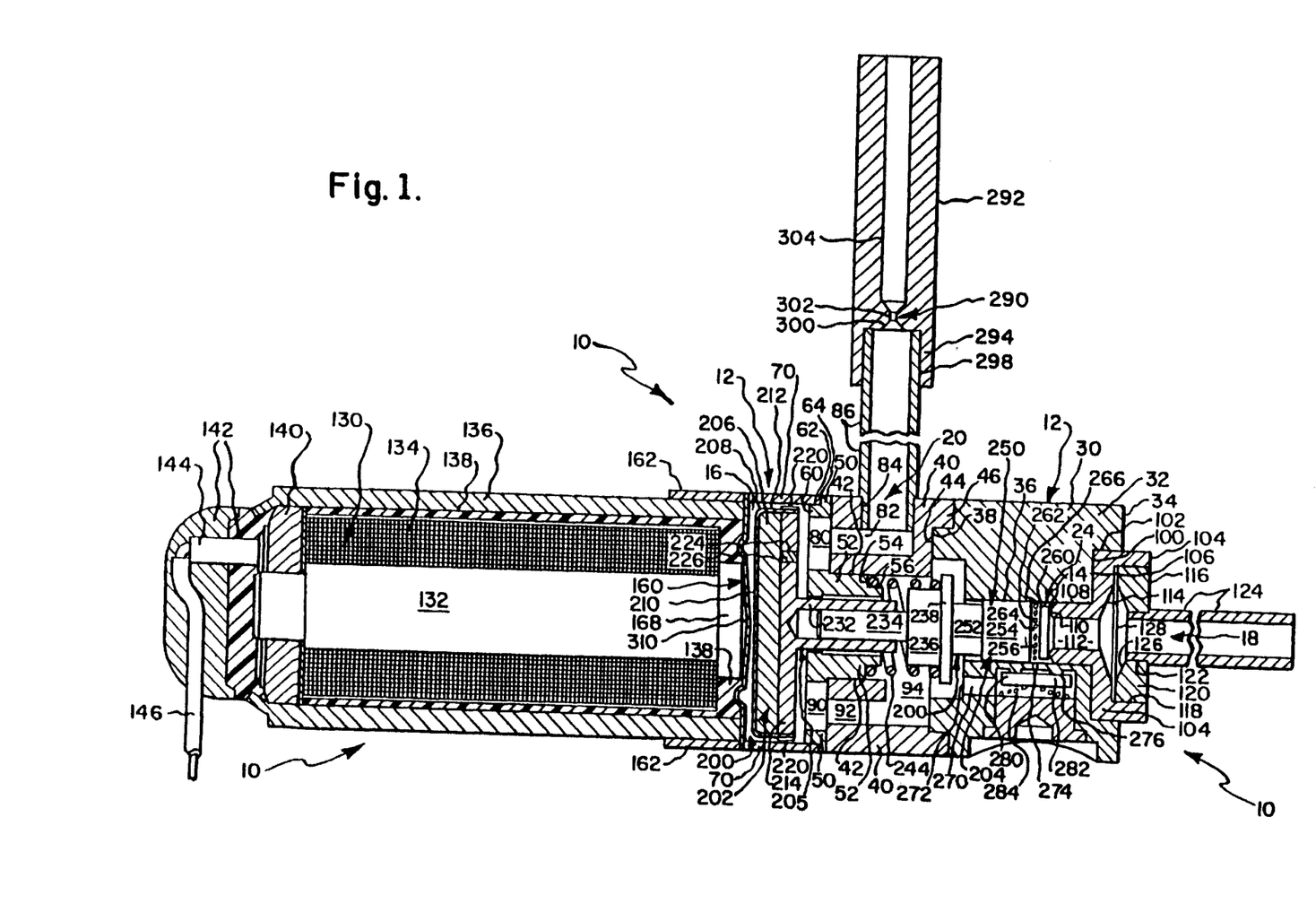
FIG. 1 is a longitudinal sectional view of a pump according to one embodiment of the present invention.

Referring now to FIG. 1, a pump 10 according to one embodiment of the present invention includes a housing 12 which is generally hollow, either rectangular or cylindrical in overall shape, and pump 10 includes an interior region for containing fluid, i.e. the liquid to be pumped. The hollow interior region includes in a manner which will be described a fluid receiving chamber 14 and a fluid output chamber 16 in fluid communication therewith. There is an inlet port generally designated 18 in fluid communication with the fluid receiving chamber 14 and adapted to be connected in the fluid handling circuit containing pump 10. There is also an outlet port 20 in fluid communication with the fluid output chamber 16 and adapted to be connected in the fluid handling circuit. In the illustrative pump shown, inlet port 18 is adapted to be connected to a source or supply of fluid to be pumped, and outlet port 20 is adapted to be in fluid communication with a location to which fluid is to be pumped. There is also provided check valve means generally designated 24 operatively associated with the fluid-containing region of pump 10 for allowing fluid flow in a direction from the inlet 18 through outlet 20 and blocking fluid flow in a direction from the outlet through the inlet. In the pump of this embodiment, check valve means 24 is within the pump and associated with the pump armature in a manner which will be described.

Housing 12 is generally hollow including a first body portion 30 of relatively substantial wall thickness. Housing 12 also includes a first axial end portion 32 extending from one end of body 30, i.e. the right-hand end as viewed in FIG. 1, and which is of relatively smaller wall thickness terminating in an axial end face 34. Housing portion 30 defines an interior region of constant diameter having an inner surface 36. The housing portion 30 terminates at the other end thereof, i.e. the left-hand end as viewed in FIG. 1, in an end face 38. Housing 12 includes a second or central body portion 40 which defines an interior region of constant diameter having an inner surface 42. Body portion 40 has a first axial end face portion 44 which contacts the end face 38 of body portion 30. An annular flange or rim 46 extends axially beyond end face portion 44 and is received in an annular shoulder defined between end face 38 and the outer surface of body portion 30. The outer surfaces of body portions 30 and 40 are of substantially equal cross-sectional shapes and dimensions so as to be substantially flush.

Housing 12 further comprises a spring retainer element 50 in the form generally of a bushing having an outer dimension substantially equal to the outer dimension of body portion 40 so as to be substantially flush therewith. Element 50 includes an axial extension 52 having an outer diameter substantially equal to the inner diameter of the body portion 40 so as to be received therein in a tight friction-like fit. Extension 52 terminates in an annular shoulder defined by axial and cylindrical surfaces 54 and 56, respectively, for providing a spring retaining function in a manner which will be described. The opposite end of element 50 terminates in an axial end face 60. An annular shoulder is defined by cylindrical and axial surfaces 62 and 64, respectively, at the peripheral junction between end face 60 and the outer surface of body 40. The shoulder receives one end of a first weld ring element 70 having an outer diameter substantially equal to the outer dimension of element 50 so as to be substantially flush therewith. Ring element 70 is welded at the one end thereof, i.e. the right-hand end as viewed in FIG. 1, to element 50 at the aforementioned shoulder thereof in a suitable manner. Ring 70 is joined at the opposite end thereof to other components of the pump housing in a manner which will be described.

Output chamber 16 is placed in fluid communication with outlet port 20 in the following manner. An axially extending opening or passage 80 is provided in the body of retainer element 50, extending axially inwardly from end face 60, and a longitudinal bore or passage 82 is provided in housing body portion 40 and terminates in a generally cylindrical chamber in registry with port 20 at the other end thereof. Housing portion 40 is provided with a radially extending bore or passage 84 into which is fitted one end of a conduit or fitting 86 which comprises a portion of the aforementioned fluid circuit and which will be described in further detail presently.

Thus, output chamber 16 is placed in fluid communication with outlet port 20 via the arrangement of passages 80, 82 and 84. Chamber 16 is placed in fluid communication with fluid receiving chamber 14 in the following manner. Another axially extending opening or passage 90 is provided in the body of retainer element 50, extending axially inwardly from end face 60 and located substantially diametrically opposite the passage 80. Body portion 40 is provided with a longitudinally extending bore or passage 92 located so as to be in fluid communication with passage 90. A radially extending opening 94 in body 40 meets passage 92 at the end thereof. As a result, the interior of body portion 40, and thus chamber 14, is placed in fluid communication with chamber 16 via the arrangement of passages 90, 92 and 94.

Inlet port 18 is provided by the following arrangement. A cylindrical recess of short axial length is provided in housing axial end face 34 and terminates in an inner annular end face 100. The inner surface 102 of the recess has a diameter larger than that of housing inner surface 36. Surfaces 100 and 102 define an annular shoulder which receives the cylindrical body of a ferrule element 104 in a tight-fitting relationship. Ferrule 104 has an inner axial end face 106 provided with a central, boss-like axial extension 108 having an axial end face provided with an annular valve formation 110 which is shaped to define a sharp annular edge facing axially into the housing interior region. A central bore or passage 112 of constant diameter extends axially inwardly from valve formation 110 whereupon it meets a passage 114 of increasing diameter. Ferrule 104 also has an outer axial end face 116 which extends axially outwardly from housing end face 34 for a short distance. A cylindrical recess 118 is formed in end face 116 and extends inwardly for about half the axial length of ferrule 104. A cap 120 having a cylindrical outer shape is received in recess 118. Cap 120 has a central opening 122 into which is fitted one end of a conduit or fitting 124 which comprises a portion of the aforementioned fluid circuit and which will be described in further detail presently. Opening 122 has an end portion 126 of increasing diameter substantially corresponding to passage 114 of ferrule 104. Thus, a flow path is defined through the central passage of cap 120 and the passage portions 112 and 114 thereby defining inlet port 18. A disc-shaped filter element 128, preferably of the etched titanium type, is fitted between ferrule element 104 and cap 120 as shown in FIG. 1 so as to be in the flow path.

The pump of the present invention further comprises electromagnet means generally designated 130 carried by housing 12 and located external to the fluid containing region of the housing. As shown in FIG. 1 the electromagnet 130 includes a core 132 in the form of a spool which is generally solid cylindrical in shape. A coil 134 is wound on spool 132 and contained within a hollow housing 136 generally cylindrical in shape. A sleeve-like body 138 of encapsulant material is between coil 134 and housing 136 and extends axially inwardly around the end of coil 136 facing housing 12. One end of electromagnet 130 is adjacent and in abutting relation to housing 12 and the opposite end, i.e. the left-hand end as viewed in FIG. 1, is closed by an arrangement including a washer 140 and a body 142 of encapsulant such as epoxy material. A pair of terminals one of which is designated 144 provide electrical connection from a power source, such as a lithium battery charging circuit and capacitor, to electromagnet 130 via a pair of conductors, one of which is designated 146. Electromagnet 130 is joined to housing 12 in the following manner.

The interior, fluid containing region of housing 12 and the electromagnet 130 are separated by a barrier means of fluid impervious material in the form of a relatively thin plate or diaphragm-like component 160. A second weld ring 162 is provided on the end of magnet housing 136 adjacent housing 12. The outer diameter of ring 162 is substantially equal to the outer diameter of the first weld ring 70 so that the respective outer surfaces are substantially flush. The region between coil 134 and barrier 160 is occupied by the annular ring portion of encapsulant 138. The housing and electromagnet structures are placed in abutting relation on opposite sides of the plate 160, and the assembly is secured together by a weld joining the respective outer surfaces of the weld rings 70 and 162. In addition, an enlarged annular end portion 168 of spool 132 contacts the central portion of plate 160 in a manner supporting the same.

The pump according to the present invention further comprises an armature generally designated 200 positioned in the fluid containing region of housing 12. The armature has a pole portion 202 located for magnetic attraction by the electromagnet 130. The armature has a piston portion 204 associated with the fluid receiving chamber 14 for moving fluid into chamber 16. The armature has the pole portion 202 for movement within chamber 16 as shown in FIG. 1. The armature 200 is movably supported in housing 12 for movement from a rest position through a forward pumping stroke when attracted by the electromagnet 130 to force fluid out through outlet 18, and for movement in an opposite direction through a return stroke back to the rest position. In FIG. 1, armature 200 is shown in the rest position at the end of the return stroke.

Armature 200 includes a shaft or rod portion 205 which is positioned in housing 12 with the longitudinal axis thereof generally coincident with the longitudinal axis of housing 12. A major portion of the length is a section of relatively small diameter. Armature 200 includes a pole portion generally designated 202 which occupies a major portion of chamber 16 in which it is located, and pole portion 202 has a lateral dimension as viewed in FIG. 1 which is several times greater than the longitudinal dimension thereof. In accordance with the present invention, pole portion 202 comprises a body of magnetic material within a titanium enclosure, the encapsulation provided by the titanium enclosure providing protection against corrosion from insulin stabilized for use in implantable delivery systems and other corrosive drugs. In particular, pole portion 202 comprises a body 206 in the form of a disc. The enclosure comprises a thin-walled cap 208 having a base 210 contacting one axial face of disc 206 and an annular rim 212 contacting the periphery of disc 206. The enclosure is completed by a disc-shaped body 214 contacting the opposite axial end face of disc 206 and abutting the rim 212 of cap 208. As shown in FIG. 1, rim 212 of cap 208 extends slightly axially beyond the periphery of disc 206, body 214 fits within and contacts rim 212, and a weld ring 220 embraces the periphery of rim 212 so that ring 220, rim 212 and the disc-shaped body 214 can be welded together at the junctions thereof.

The disc-shaped body 214 is provided with at least one vent passage 224 therein to evacuate residual gas during assembly, the passage 224 being sealed by a plug 226 after assembly. Passage 224 is in the form of an axially extending through bore in body 214. The provisions of passage 224 and plug 226 is necessary because the small residual volume of gas within cup 208 must be evacuated to hold cup 208 tight against disc 206 even when the interior of pump 10 is at low pressure. Plug 226 is in the form of a filler pin and is welded in place with the entire assembly under vacuum to close the vent hole 224 in body 214.

Thus, the armature pole portion 202 terminates at the end facing electromagnet 130 in an axial end face which serves as the pole face and is disposed substantially perpendicular to the armature axis. The armature pole face together with electromagnet 130 define the magnetic circuit gap which is closed during the forward armature stroke. The pole face is of relatively large cross-sectional area as compared to the cross sectional area of the armature piston portion 204. The armature pole portion 202 serves as the plunger portion of the armature, and as the pole face moves toward plate 160 when magnet 130 is energized, pole portion 204 upon moving toward chamber 16 displaces fluid and moves it toward outlet 20.

Armature shaft portion 205 is joined to the pole portion 202 via a sleeve-like axial projection or bushing 232 extending from disc-shaped body 206 to which is attached an armature rod or shaft 234. The outer diameter of bushing 232 is slightly smaller than the inner diameter of retainer element 50 so that bushing 232 is freely longitudinally movable along within retainer 50. The attachment is made by crimping the bushing 232 which allows the overall length of the piston assembly to be changed to adjust the piston stroke. Shaft 234 is provided with an enlargement at the end opposite bushing 232 which includes two relatively larger diameter shaft sections. In particular, there is a first section 236 facing bushing 232 and a second, axially adjacent section 238 which is larger diameter. The section 236 is of relatively shorter axial length, and the sections 236, 238 define therebetween a shoulder facing pole portion 204.

There is provided biasing means in the form of a coil spring 244 for urging armature 200 toward the rest position shown in FIG. 1. One end of spring 244 seats in the annular shoulder defined by the armature shaft sections 236, 238. The opposite end of spring 244 seats in the annular shoulder defined by surfaces 54, 56 of retainer element 50 previously described. Retainer 50 is concentric with the armature shaft portion 202 and receives spring 244 which also is concentric with armature shaft portion 202. As previously described, the armature shaft portion 202, in particular bushing 232, is freely axially movable within retainer 40.

Armature 200 includes a piston generally designated 250 movably positioned within the interior region of housing portion 30 and extending axially from armature body portion 238 toward inlet 18. Piston 250 is substantially cylindrical in shape having a first section 252 axially adjacent body portion 238 of relatively smaller diameter for a purpose to be described and a second section 254 of diameter slightly larger than section 252. Section 254 also is of greater axial length as compared to section 252. The outer diameter of section 254 is slightly less than the diameter of the interior passage in housing portion 30 to allow reciprocal movement of piston 250 within housing portion 30 during the forward and return strokes of armature 200. Section 254 terminates in an axial end face 256 which faces toward inlet 18.

The pump according to the present embodiment includes check valve means 24 operatively coupled to the armature 200 and located in the fluid-receiving region of the housing for operating and closing the pump inlet. In particular, the check valve means 24 comprises a valve member positioned and biased for closing the pump inlet when the armature is in the rest position and allowing opening of the inlet after the armature begins movement associated with the forward pumping stroke. In the embodiment of FIG. 1, check valve means 24 is located in the fluid-receiving chamber 14 between inlet 18 and the armature piston end face 256. Check valve means 24 includes a body or seat 260 in the form of a disc having a surface facing and adapted to sealingly contact the edge of the valve formation 110, a backing element or plate 262 contacting disc 260, a shim 264 contacting armature end face 256, and a biasing spring 266 in the form of a conical spring between backing element 262 and shim 264. The valve seat 260 is loosely positioned in the passage and is relatively thin. As a result, seat swelling caused by temperature changes or the presence of various liquids has a smaller effect on the liquid volume delivered per stroke. This seat structure makes it possible to reduce the clearance between seat 260 and the passage in housing portion 30. The small clearance and thinner seat 260 together contribute significantly to reducing the volume of the fluid-receiving chamber 14 with armature 200 in the rest position. The backing element 262 provides a bearing surface for spring 266 at all times and when armature 200 is at rest. The biasing spring is compressed to an approximately flat configuration as shown in FIG. 1 when armature 200 is in the rest position. The arrangement and structure of check valve means 24 and the provision of conical spring 266 minimizes the internal volume of the receiving chamber 14 thereby limiting the maximum size of a bubble which can be contained therein.

The pump of the present invention further comprises a bypass passage in the pump body between the pumping chamber 16 and the fluid receiving chamber 14 to provide a path for bubbles and fluid around the armature piston, which is closely movably fitted within the pump body, and check valve means in the bypass passage which opens during the return stroke of the armature 200. The need for the bypass path arises from the small clearance between piston section 254 and the passage in housing portion 30 requiring a potentially high pressure difference to force bubbles therethrough and the possibility of a bubble becoming trapped between piston section 254 and the passage and inhibiting further pumping or in an extreme case preventing return of armature 200. In particular, housing portion 30 is provided with a longitudinally extending bore or passage 270 radially offset from the central interior passage and extending axially inwardly from an end face 272 a distance beyond the center of body 30. A radially extending bore or passage 274 places passage 270 in communication with the central interior passage substantially mid-way between the axial ends of housing portion 30. In accordance with the present invention, passage 274 is of relatively small diameter to function as a bypass orifice means to decelerate the flow rapidly at the end of the pump stroke to thereby reduce the inertial flow volume in a manner which will be described. At the junction of passages 270 and 274 there is provided an annular valve seat surface 276 formed in body 30. A check valve generally designated 280 normally blocks communication between passages 270 and 274. Check valve 280 includes a disc-shaped body or seat 282 having one surface contacting the annular valve seat surface 276 and a conical biasing spring 284 between valve body 282 and a plug 286 fitted in body 30.

The bypass check valve 280 provides a different path for bubbles past the armature piston portion 250. It is designated to open at a pressure head well below the pressure generated by the armature return spring 244. Preferably, the opening pressure for check valve 280 is also lower than the bubble point of the gap between piston section 254 and the passage. The provision of bypass check valve 280 causes a rapid return stroke of armature 200, since the armature return no longer is limited by the rate of fluid leakage between armature piston 250 and the passage. Instead the major part of the fluid moves from output chamber 16 along passage 270 through check valve 200 and passage 274 into chamber 14 along with any bubbles contained in the fluid.

The provision of bypass check valve 280 as an alternate bubble path offers two principal advantages. First, it reduces the dependence of the pump behavior with bubbles present upon the fluid surface tension, the surface properties of armature piston 250 and the interior passage of housing portion 30, and the clearance between piston 250 and the passage. Second, and perhaps more important, it preserves the continuity of the liquid film between piston 250 and the passage of body 30 during bubble passage, which liquid film plays an important role in operation of the pump.

In accordance with the present invention, there is provided means generally designated 290 for providing an orifice in the path of fluid flow from pump outlet 20 so as to reduce the effect of the momentum of the fluid stream through the pump 10 on the volume of fluid delivered during each pump cycle. This will be described in further detail presently. In the pump of the present illustration, the outlet conduit or fitting 86 which extends from outlet 20 provides a path for fluid flow from pump 10 and comprises a relatively rigid tubing. One end of tubing 86 is connected to pump outlet 20 and the orifice providing means 290 is located adjacent the other end of tubing 86. In particular, a length of relatively rigid outlet tubing 292 is provided with one end 294 tightly fitted on or otherwise properly secured to the end of fitting 86. Tubing 292 can be of any required length and the other end is located at a point of use for the fluid being pumped. Within the tubing end 294 there is an inner section 298 having a diameter substantially equal to the outer diameter of fitting 286. Section 298 extends axially inwardly a relatively short distance where it meets a radially inwardly extending wall portion 300 which is provided with a small diameter central bore or passage 302 providing the aforementioned orifice. Wall portion 300 includes inwardly tapering surfaces so that passage 302 is of relatively short axial length. The remainder of the axial length of tubing 292 has a constant diameter inner section 304 which in the present illustration is of smaller diameter than section 298.

In operation, inlet 18 is connected to a source or supply of fluid to be pumped, and outlet 20 is connected via tubing 292 to a point or location of use for the pumped fluid. The armature 200 is moved through a forward pumping stroke in response to electrical energization of electromagnet 130. One way of energizing magnet 130 is to charge a capacitor from a battery and then discharge that capacitor through coil 134. Other procedures can of course be employed for electrically energizing coil 134 in a known manner. Prior to electrical energization of magnet 130, armature 200 is in the rest position illustrated in FIG. 1 where the check valve 240 is located with the surface of body 260 seated against the edge of valve formation 110 surrounding the opening of the inlet fitting passage to block fluid communication from inlet 18 to the fluid receiving chamber 14. In the rest position of armature 200, pole portion 202 is spaced from diaphragm 160 as shown in FIG. 1 thereby defining the gap in the magnetic circuit. In the rest position, this gap between pole portion 202 and diaphragm 160 is of maximum length.

When coil 134 is electrically energized, the armature pole portion 202 is attracted toward magnet 130 thereby causing armature 200 to be drawn toward diaphragm 160. Electromagnetic flux travels through the magnetic circuit including the electromagnet core 132, washer 140, magnet housing 136, the included portion of the periphery of diaphragm 160 between the end face of housing 136 and cap 208, armature pole body 206, and the gap between the armature pole face and diaphragm 160. As armature 200 is moved in the forward pumping stroke, i.e. in a direction to the left as viewed in FIG. 1, the armature pole portion 202 moves further toward diaphragm 160 thereby decreasing the gap in the magnetic circuit. During the forward pumping stroke of armature 200 the flow through passages 92 and 90 is approximately equal to the difference between the cross sectional areas of the piston 250 and ferrule 232 multiplied by the stroke length and this is about one-half the pump displacement. The remaining one-half of the displacement passes through passages 92 and 90 during the return stroke of the pump. During the forward pumping stroke the flow passing from chamber 16 into outlet 20 is partly driven by flow through passages 92 and 90 and partly by the displacement of ferrule 232 as it extends farther into chamber 16. Thus, fluid is forced out through passages 80, 82 and 84 through the outlet 20. Accordingly, because the internal volume of pump 10 does not change during a pumping stroke, fluid flows into inlet 18 and out of outlet 20 simultaneously with the forward motion of the plunger. The bypass circuit allows flow around piston 250 during the plunger return stroke, while backflow is prevented by check valve 24.

The check valve 24 moves freely with respect to the armature 200 and does not necessarily move when the armature 200 is drawn toward diaphragm 160. At rest, the surface of check valve body 260 is held in contact with the edge of the valve formation 110 by the spring 244 acting upon the armature 200 which is then in contact with check valve body 260 and the compressed spring 266. When the armature 200 is drawn toward diaphragm 160, the force of spring 244 is no longer transferred to the check valve 24 and the force holding the surface of check valve body 260 against the valve formation 110 is decreased to that provided by spring 266, which generally provides a force less than that provided by spring 244. If armature 200 is drawn toward electromagnet 130 with sufficient velocity, pressure within the pump housing 12 between the end face of piston 250 and the check valve body 260 decreases to a level below the level at the pump inlet 18, and the net force due to fluid pressure from inlet 18 acting on the check valve 24 tends to move the surface of check valve body 260 away from contact with the end of the inlet fitting. If the net force due to the fluid pressure exceeds that provided by the spring 266, then check valve 24 moves away from the inlet fitting and fluid flows into the pump body. In fact, because the fluid is nearly incompressible the check valve 24 opens at approximately the same time that the armature 200 achieves enough velocity to force fluid out of the pump outlet 20. The forward pumping stroke of the armature 200 is completed when the armature pole face approaches contact with the diaphragm 160. When the armature velocity decreases to a level such that the displacement rate of the motion of the pole portion 202 no longer exceeds the leak rate between the outer surface of armature piston section 250 and the central interior passage of housing portion 30, the pressure within the pump housing 12 begins to increase. When the force due to the pressure difference across the check valve 24 no longer exceeds the force of spring 266, the check valve member 260 moves toward the valve formation 110 and prevents flow out of the inlet port 18 of the pump.

Thus, during the forward pumping stroke there is a reduction in the internal volume of the pump downstream of piston 250, and there is a corresponding increase in the internal volume of the pump upstream of piston 250. During the forward pumping stroke bypass check valve 280 is closed. Therefore, during the forward pumping stroke fluid flows in through pump inlet 18 to fill the increased internal volume upstream of piston 250, and fluid flows out through pump outlet 20 to accommodate the decreased internal volume downstream of piston 250. Thus, the internal volume of the pump on the downstream side of piston 250 is a pumping chamber.

When electrical excitation of coil 134 ceases, armature 200 is moved in the opposite direction, i.e. to the right as viewed in FIG. 1, by the force of biasing spring 244 until the armature reaches the rest position as shown in FIG. 1. During the return stroke the bypass check valve 280 is open with the result that the return motion of armature 200 is relatively rapid as previously described. During the return stroke of armature 200, check valve 24 is held against valve formation 110 primarily by the force of spring 266 supplemented by the difference between the outlet and inlet pressures acting on the check valve seat. When the return stroke is completed the spring force is increased to that of spring 244. The average pumping rate is determined by the rate of return of armature 200 to the rest position. Thus, the relatively rapid return of armature 200 provided by bypass check valve 280 increases the maximum available pumping rate. Armature 200 remains in the rest position of FIG. 1 with inlet 18 closed and waiting for the next forward pumping stroke which occurs when magnet 130 is energized again.

Thus, during the return stroke of armature 200, the check valve 24 is closed and bypass check valve 280 is open. The internal volume upstream of piston 250 decreases, and excess fluid is removed from that volume through bypass check valve 280. The internal volume downstream of piston 250 increases, and fluid is supplied to that increased volume by the flow of fluid through bypass check valve 280.

The surface of barrier 160 facing armature 200 is provided with a slightly conical shape with the apex or tip 310 of the cone pointing toward or facing armature 200. The cone thus defined is very blunt and nearly flat, the angle of the cone measured relative to the longitudinal axis of pump 10 being approximately 89°. The taper of this conical surface of barrier 160 is sufficient to change the behavior of the armature 200 during the return stroke thereof as compared to a completely flat or planar surface of barrier 160. In particular, the conical surface of barrier 160 is believed to reduce the pressure difference at the armature pole face which may occur if a gas-liquid interface should encircle the armature pole face surface in contact with barrier plate 160. Such a gas-liquid interface could otherwise support a pressure difference at the armature pole face sufficient to overcome the force of armature return spring thereby slowing or interfering with the return stroke of armature 200. Thus, the conical surface of barrier 160 serves to reduce the force which may under certain circumstances hold the armature pole face close to the barrier 160 in the presence of a liquid-gas interface. The conical surface of barrier 160 also serves to decrease the time required for the armature pole face to separate from the barrier 160 at the beginning of the plunger return stroke. This is a viscous flow effect and occurs even if no liquid gas interface is present.

Long term sealing is provided by the relatively stronger spring 244, and short term sealing while armature 200 is forward is provided by the relatively weaker spring 266. As a result, there can be satisfactory sealing against the back flow when the pump is not in operation, while the pressure drop across the check valve 24 during the pump stroke is small.

The relatively smaller diameter of armature piston 250 as compared to pole portion 202 allows it to pump against higher back pressures without saturating the existing magnetic circuit. An additional advantage of this configuration is that for a given stroke volume, the smaller diameter of piston 250 allows that the linear stroke be longer. This tends to improve the stability of the stroke volume since the effect of seat swelling or stroke volume is smaller. Another advantage arises from the fact that the volume of the pump chamber 14 with armature 200 in the rest position is smaller for the smaller combination of piston 250 and the passage in housing portion 30.

The smaller diameter section 252 of piston 250 provides a necking down of the piston at its downstream end for the purpose of reducing the tendency of a bubble to be drawn back into the clearance between armature piston 250 and the passage in housing portion 30. As previously mentioned, continuity of the liquid film in this clearance is important to operation of pump 10. The film maintains the required pressure drop on opposite sides of piston 250 during the pumping stroke, and a gas bubble in that clearance could provide a leak thereby tending to equalize pressure on opposite sides of piston 250. The necked down section 252 of piston 250 provides a route by which liquid may move around a bubble in the space between section 252 and the passage in housing portion 30 and thereby move into and along the gap between piston section 254 and the passage in housing portion 30. The pump 10 according to the present invention thus has the capability of operating with bubbles in the inlet stream.

The foregoing provisions for improving the bubble pumping capability of pump 10 can, however, lead to what may be designated the inertial effect. When the pump armature 200 reaches the end of its stroke, the momentum of the fluid stream can cause the flow through pump 10 to continue for a short time. The volume flow through pump 10 during a single stroke may therefore be greater than the displacement of the armature piston portion. At the end of a stroke the flow decelerates more rapidly if pump 10 is pumping against a large positive pressure difference than it does if the pressure difference is small or negative. The volume pumped per stroke therefore increases as the backpressure decreases. The desired pumping characteristic, however, would have pump 10 delivering a constant volume per stroke independent of the delivery pressure.

In accordance with the present invention, it has been found possible to reduce the inertial flow volume in pump 10 by providing orifices of small diameter in the flow path to decelerate the flow rapidly at the end of the pump stroke. Two orifice locations are determined to be appropriate, the orifice 274 in the bypass leg of the flow through pump 10 and the orifice 302 at the downstream end of the rigid tubing 292 on the outlet side of pump 10.

The bypass orifice location has the advantage that the orifice 274 does not affect the flow during the pump stroke. In particular, bypass check valve 280 is closed during the forward pump stroke and there is no flow through the bypass orifice 274 until the pump stroke is complete. Immediately after the end of the forward pump stroke, the flow, now driven by the momentum of the fluid stream, is diverted primarily through the bypass orifice 274. A small part of the flow passes through the small clearance between the armature piston 250 and housing portion 30. The pressure drop of the flow through the orifice 274 then combines with the pressure drop through the remainder of the system to decelerate the flow and limit the inertial flow volume. During the plunger return stroke a volume of flow approximately equal to the volume displaced by the piston stroke passes through the bypass orifice 274 and check valve 280. The pressure drop through the bypass orifice 274 during the plunger return stroke is not important, however, since the plunger return stroke need not be particularly rapid.

Thus the location of orifice 274 in the bypass circuit is favorable with respect to pump operation at normal conditions. It does not in any way change the flow during the actual pump stroke because the bypass check valve 280 is closed at that time. Accordingly, the provision of orifice 274 is an effective means for reducing the inertial flow volume. Orifice 274 is located between the pump chamber and the bypass check valve 280. Because the inertial flow is sensitive to the pressure increase across pump 10, reduction of the inertial flow volume can be expected to reduce the sensitivity of the overall pump pulse volume to back pressure. By way of example, in an illustrative pump having a normal pulse volume in the range from about 0.4 $\mu$L to about 0.6 $\mu$L, providing orifice 274 with a diameter of about 0.005 inch has been found to produce satisfactory results.

The downstream orifice location has the effect that the main flow must pass through orifice 302 during the actual pump stroke. There is therefore a substantial pressure drop in the flow during the actual pump stroke which may extend the time duration of the actual pump stroke and increase required energy of the driving electrical impulse. As a result of the extended stroke time and the possibly increased pressure difference across the armature piston 250, the flow leakage around the piston 250 may increase thereby tending to decrease pump accuracy. However, it has been determined according to the present invention that although the potential problems of flow leakage and energy increase exist, the downstream orifice 302 of proper size can increase the accuracy of a pump tubing combination without imposing a significant performance penalty. In this connection, it has also been determined according to the present invention that downstream orifice 302 is particularly effective in controlling the inertial effect associated with rigid or non-compliant tubing in the flow path from the outlet of pump 10. The downstream orifice 302 ensures that fluid pressures within pump 10 remain positive during deceleration, and orifice 302 provides a mechanism for decreasing the fluid stream rapidly thereby reducing its momentum. Thus, in accordance with the present invention, it has been determined that orifice 302 installed at the downstream end of any hard, i.e. non-compliant, tubing which must be attached directly to pump outlet 20 offers an effective solution to the problem of flow inaccuracy due to inertial effects. By way of example, in an illustrative pump having a normal pulse volume in the range from about 0.4 $\mu$L to about 0.6 $\mu$L, providing orifice 302 with a diameter of about 0.005 inch has been found to provide satisfactory results.

Since the armature pole body 206 is completely enclosed within cap 208 and disc 214 of material which is compatible with and corrosion resistant to the fluid being pumped, the magnetic material for body 206 can be chosen without concern for corrosion resistance. A 4750 nickel-iron alloy for body 206 has been found to provide satisfactory results.

Pump 10 accordingly has the advantages of operating at extremely low power levels, being compatible with drugs and similar liquids to be pumped, being electrically and magnetically efficient, being small in size, light in weight and reliable in operation, having the capability of operating with bubbles in the input liquid stream, and reducing the fluid inertial effect on pump accuracy.

The non-movable diagram 160 of titanium or like material provides an hermetic seal between the fluid in housing 12 and the electrical components associated with electromagnet 130. Having armature 200 immersed in the fluid makes operation of the pump nearly independent of ambient pressure. The initial condition of the pump 10 when armature 200 is in the rest position of FIG. 1, is that fluid is at substantially the same pressure on opposite sides of the armature pole portion 202, i.e. in the two chambers 14 and 16.

The pump 10 of the present invention is made electrically and magnetically efficient by minimizing the total gap within the magnetic circuit, by having the magnetic pole face of armature pole portion 202 of relatively large surface area, and by having core 132 of relatively small cross-sectional area. In particular, there is a relatively significant contact area at the interface between the axial end face of magnet housing 136 and diaphragm 160 to minimize the effective air gap introduced by diaphragm 160 at this point in the magnetic circuit. In other words, diaphragm 160 is relatively thin in relation to the aforementioned contact area. Related to this is the need for welding diaphragm 160 to rings 70 and 162 to achieve an hermetic seal between electromagnet 130 and the fluid containing region of housing 12 while at the same time not adversely affecting the magnetic circuit. The relatively small diameter of core 132 provides the necessary number of ampere turns with a minimum electrical resistance. The large area of the pole face of the disc-shaped armature pole portion 202 provides a high magnetic force with a minimum number of ampere turns. Having the magnetic gap external to coil 134, i.e. between the armature pole face and diaphragm 160, allows the foregoing features to be achieved simultaneously.

Figure 2:
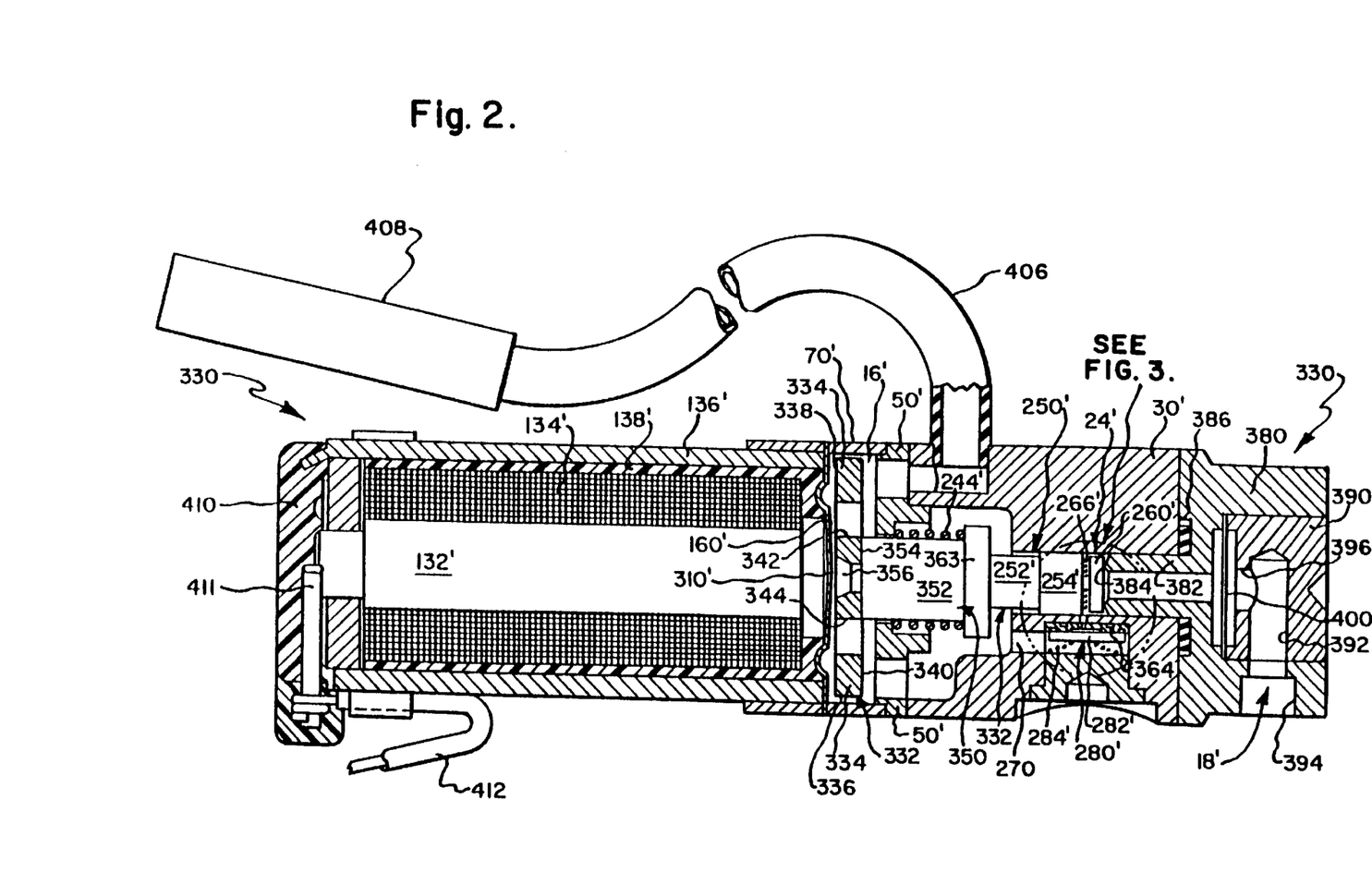
FIG. 2 is longitudinal sectional view, partly in eluation, of a pump according to another embodiment of the present invention.
Figures 3, 4, 5:
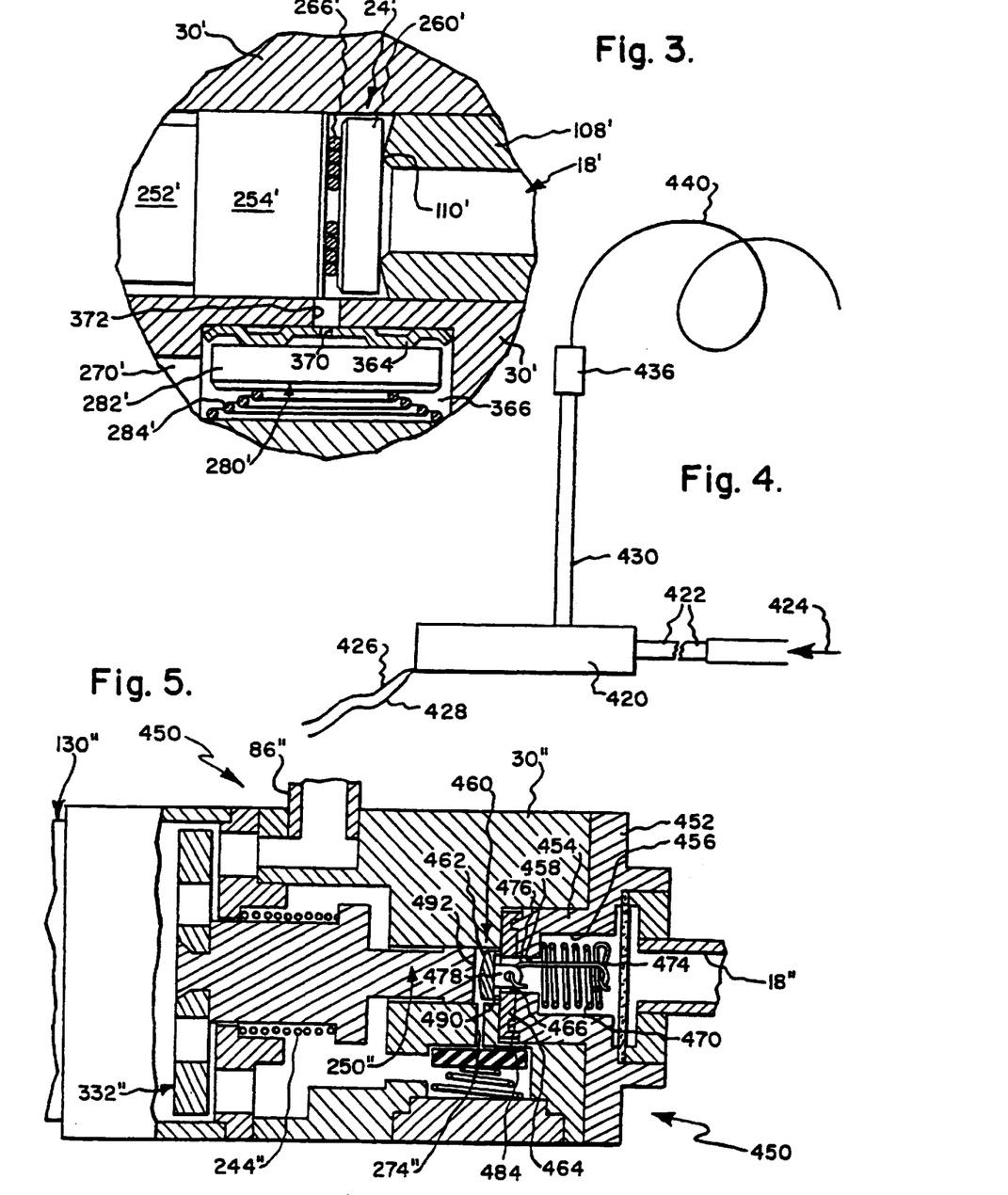
FIG. 3 is an enlarged view taken within the region in FIG. 2 outlined by dotted lines.
FIG. 4 is a fragmentary side elevational view, partly diagrammatic, illustrating a pump arrangement according to another embodiment of the present invention.
FIG. 5 is a fragmentary longitudinal sectional view of a pump according to another embodiment of the present invention.

FIGS. 2 and 3 show a pump 330 according to another embodiment of the present invention. Components of pump 330 similar to those of pump 10 are identified by the same reference numeral with a prime designation. A principal difference between the two embodiments is that armature 332 in pump 330 is simpler in structure and relatively easier to manufacture and assemble. In particular armature 332 has a pole portion 334 comprising a solid, monolithic body having the shape or form of a disc. The lateral dimension of pole portion 334 is several times the longitudinal dimension thereof. Pole portion 334 has a first axial end face 338 which faces toward barrier means 160' and a second, opposite axial end face 340 which faces toward inlet port 18'. Thus, end faces 338, 340 are disposed substantially perpendicular to the direction of travel of armature 332.

Pole portion 334 is exclusively of magnetic material, preferably a chrome-molybdenum-iron alloy which is heat treated. Examples are 29-4 and 29-4C chrome-molybdenum iron alloy. This alloy has high corrosion resistance, and has adequate magnetic characteristics for use in pump 330 when heat treated. In other words, the alloy is heat treated to provide a BH characteristic for the alloy which yields the requisite level of magnetic flux density and coercive force. Furthermore, the alloy is sufficiently resistant to corrosive effects of insulin stabilized for use in implantable drug delivery systems as well as other corrosive drugs.

In particular, the afore-mentioned chrome-molybdenum-iron alloy is a ferritic stainless steel alloy containing 29% chromium, 4% molydenum and the remainder substantially iron. The afore-mentioned heat treatment involves an anneal and rapid cool of the armature pole portion 334. In particular the procedure involves a short magnetic anneal at a temperature above that which can form a harmful second phase in the alloy followed by cooling rapidly enough to avoid second phase formation but not so rapidly as to degrade magnetic properties. Heating of armature pole portions 334 of 29-4 alloy is performed for example in a clamshell furnace at a temperature of about 1010° C. for about twenty minutes whereupon the parts 334 are removed quickly to the ambient in a manner allowing complete cooling for a minimum of 25 minutes. The cooling rate during the first portion of the cooling cycle from 1010° C. down to black, i.e. down to 600° C., should be maintained at about 60 seconds.

The armature body or pole portion 334 is provided with at least one passage means therethrough, and in the pump shown two axially extending through bores or passages 342, 344 are shown. The passages 342, 344 extend through the entire axial length of armature body 334 between the axial end faces 338, 340. Passage means 343, 344 serve to reduce the time required for armature pole portion 334 to separate from barrier means 160' during movement of armature 332 toward port 18' and to reduce surface tension effects between barrier means 106' and pole portion 334. The path for fluid flow defined by passage means 342, 344 provides the foregoing results when energization of electromagnet 130' ceases and the force of spring 244' begins to move armature pole portion 334 away from barrier means 160'. In addition, barrier 160' is provided with a central conical formation identical to that of barrier 160 in the embodiment of FIG. 1 and which functions in an identical manner for the same purpose.

Thus, the one-piece pole portion 334 of armature 332 contributes to the simplicity in structure and ease of manufacture and assembly. These advantages also result from the provision of an armature shaft portion 350 which simply is fastened at one end to the pole portion 334. In particular, armature shaft portion 350 comprises a rod-like body 352 having an axial end face 354 which abuts the axial end face 340 of pole portion 334. A rivet 356 or similar fastening means is employed to simply attach shaft portion 350 to pole portion 334. The outer diameter of rod 352 is slightly smaller than the inner diameter of spring retainer 50'. Armature shaft portion 350 meets an annular enlargement 360 which defines with the adjacent portion of shaft 350 an annular shoulder for receiving one end of biasing spring 244'. The remainder of the armature comprises piston portion 250' including the first and second sections 252' and 254', respectively, wherein section 252' meets enlargement 360. The foregoing armature structure avoids problems involving criticality of alignment during assembly of pump 330.

Pump 330 illustrates an alternative arrangement for providing an orifice in the fluid bypass path. In particular, the orifice providing means comprises a plate-like element 364 having a central through bore to define the bypass orifice. Referring to the enlarged view of FIG. 3, element 364 is of metal in the shape of a disc and is force-fitted or otherwise suitably secured in a chamber 366 formed at the end of passage 270'. Element 364 is located in chamber 366 so as to serve also as a valve seat for by-pass check valve 280'. A small diameter bypass orifice 370 is drilled or otherwise provided generally centrally of element 364, and orifice 370 is in fluid communication with a radially extending bore or passage 372 leading from the central passage in housing portion 30'. Providing bypass orifice 370 in element 364 has the advantages of ease and accuracy of forming orifice 370 together with the ability to change the size of orifice 370 upon removal of element 364 and replacing it with a new or re-machined element having a different size orifice.

In pump 330 of FIGS. 2 and 3, inlet 18' is provided by an arrangement including an inlet fitting 380 in axially abutting relation with the end face of housing portion 30' and having a central boss-like extension 382 which terminates in an annular valve formation 384. A sealing ring 386 seated in a recess in the inner end surface of fitting 380 provides a fluid seal between fitting 380 and housing portion 30'. This is particularly useful during testing of pump 330 prior to joining fitting 380 to housing portion 30'. A central recess in the outer end face of fitting 380 receives a filter plug element 390 provided with a laterally extending bore or passage 392 in communication with an inlet port opening 394 provided in the wall of fitting 380. A relatively short longitudinally extending bore or passage 396 in element 390 places passage 392 and thus inlet port 394 in fluid communication with the central passage in housing portion 30'. A disc-shaped filter element 400, preferably of the etched titanium type, is located between fitting 380 and plug 390 and in the fluid flow path. Thus, the foregoing arrangement allows for a right angle connection of an inlet conduit to pump 330. In the illustrative arrangement of FIG. 2, the pump outlet 20' in connected to one end of a flexible tubing or conduit 406, the other end of which is connected to an outlet fitting representing generally at 408.

The left-hand end of pump 330 as viewed in FIG. 2 is closed by a cap or closure element 410 of epoxy material in which is embedded a terminal post 411, one end of which is in contact with the axial end of core 132' and the other end of which is connected to an electrical cable 412. Pump 330 operates in a manner similar to pump 10 shown in FIG. 1.

In an implantable drug delivery system, the catheter used to lead the drug from the pump to the infusion site may be of relatively long length and small diameter and also be of low compliance. With catheters of the smallest probable diameters, the catheter could offer such high resistance to the flow during the pump stroke that the performance of a pump in such a system could be degraded seriously. With catheters of somewhat larger diameters, the steady state flow resistance would be small but the rigid catheter would lead to a very large fluid inertial effect. Although it would in principle be possible to install an orifice at the end of the catheter downstream from the pump, it would nevertheless be difficult to reduce the inertial volume to an acceptable level without again degrading the pump performance. Therefore, in accordance with the present invention, a small accumulator is provided downstream of the pump outlet orifice large enough to contain the pulse volume of the pump with a reasonable pressure rise. The catheter diameter may then be small enough to ensure that the flow through the accumulator catheter combination is critically damped and no flow oscillations occur which might otherwise draw additional flow through the pump check valves. It is desirable that the accumulator be small enough so that a significant pressure rise occurs during the pump stroke. The back pressure build-up serves the purpose of preventing a large pulse volume when the supply pressure exceeds the delivery pressure.

Such an arrangement is shown in FIG. 4 wherein component 420 is a pump according to the present invention such as pump 10 of FIG. 1 or pump 330 of FIGS. 2 and 3. An inlet tube 422 connects the inlet port of pump 420 with a source of fluid (not shown) wherein arrow 424 indicates the direction of fluid flow in the system. A pair of electrical leads 426, 428 connects pump 420 to an appropriate power source (not shown) as previously described. The arrangement further indicates an outlet tube 430, one end of which is connected to the outlet port of pump 420 and the other end of which is connected to one end of an accumulator 436. The other end of accumulator 436 is connected to one end of a catheter 440, the other end of which is connected to a liquid infusion site (not shown). In the arrangement of FIG. 4, outlet tube 430 is relatively rigid and accumulator 436 is in the form of a small compliant element. For example, accumulator 436 can comprise a small length of silicone rubber tubing, i.e. about ½ inch in length and 1/32 inch inner diameter in an illustrative arrangement. Pump 420 can include an outlet orifice like that of pump 10, a bypass orifice like that of either pump 10 or pump 330, or both an outlet orifice and bypass orifice.

In accordance with the present invention, it has been determined that the catheter-accumulator combination as shown in FIG. 4 should accomplish the following objectives. The accumulator 436 should be compliant enough to receive the entire volume of a single pump stroke with a pressure increase which is low enough so that pump operation is not disturbed. This is not a difficult requirement because the pump plunger is already partly pulled in before a significant back pressure develops in the accumulator 436, and in that position an increased magnetic force is available to the pump plunger. The compliance of the accumulator 436 should be low enough so that some moderate back pressure builds up within the accumulator during a pump stroke. This has the effect of allowing the pump 420 to operate more accurately with forward pressure differences by providing a temporary pressure rise across the pump to help decelerate the inertial flow.

Another objective is that the diameter of catheter 440 should be large enough so that the volume of a single pump stroke is completely discharged from the accumulator 436 in the interval between pump pulses. Also, the dimensions of catheter 440 and the compliance of accumulator 436 should be such that oscillations of the catheter-accumulator combination are critically damped or overdamped by viscous flow through the catheter 440.

Thus, to summarize the foregoing, accumulator 436 should be large enough to receive the volume of a single stroke of pump 420 with a pressure increase no greater than a predetermined maximum amount. Accumulator 436 should be small enough so that the pressure increases by at least a predetermined minimum amount during the stroke of pump 420. Catheter 440 should discharge its contents completely between strokes of pump 420. The combination of catheter 440 and accumulator 436 when considered independent of pump 420 should be critically damped.

FIG. 5 illustrates a pump according to the present invention which delivers a reduced stroke volume of fluid as compared to the pump of FIGS. 1–3 and which has the ability to continue operation with bubbles present in the fluid flow. Generally a reduction in the displacement of a pump of the type shown in FIGS. 1–3 would be accomplished by reducing either the length of the plunger stroke or the piston diameter. Reducing the length of the plunger stroke would reduce the displacement while leaving unchanged the rest volume of the pump chamber (bounded by the piston face and the two check valves). This would reduce the pressure head against which a bubble (assumed to fill the volume of the pump chamber) could be pumped, and this reduction can be predicted fairly accurately. If the displacement is reduced by reducing the piston diameter, however, then the rest volume of the pump chamber is reduced approximately in proportion to the reduction in the stoke volume and the bubble pumping capability should be changed very little. In this case, however, a practical problem arises with the design and fabrication of the conical main check valve spring. It becomes very difficult to obtain the low spring constant and large extension required of that spring while reducing its outside diameter below that used in pumps of the type shown in FIGS. 1–3.

The ability of a solenoid piston pump of the type shown in FIGS. 1–3 to continue pumping against a pressure head with bubbles in the fluid stream depends primarily upon the maintenance of a liquid seal between the armature piston and surrounding passage, the pressure drop across the two check valves, and the volume of the bubble captured in the pump chamber relative to the volume of the pump stroke. The term pump chamber is intended to include the interior region of the pump housing between the main check valve, the bypass check valve and the piston face. Experience has shown that the fluid seal is relatively durable so long as the pump is wet. The most important variable is therefore the volume of the trapped bubble. During passage of a large bubble through the pump the entire rest volume of the pump chamber can be expected to be filled with gas. The rest volume is the volume of the above-defined pump chamber when the armature is at the rest. Reduction of the bubble volume therefore depends primarily on the rest volume of the pump chamber, and the rest volume in pumps of the type shown in FIGS. 1–3 depends strongly upon the design of the main check valve. Therefore, in accordance with the present invention the small displacement pump 450 shown in FIG. 5 has a main check valve configuration which allows a significant reduction in the rest volume of the pump chamber. In particular, the check valve spring is located external to the pump chamber so that the rest volume of the pump chamber can be significantly reduced. The motivation for the change in the check valve design is in part to achieve a reduction in the rest volume of the pump chamber but it is also necessary in order to overcome the difficulty of making a check valve spring having the required characteristics while fitting into the reduced diameter space.

The pump 450 of FIG. 5 includes a housing, armature and electromagnet means identical to those of the pumps in FIGS. 1–3. Accordingly, components in the pump 450 identical to those in the pumps of FIGS. 1–3 are identified by the same reference numerals provided with a double prime designation. Inlet 18" is defined by a ferrule element 452 which abuts the axial end face of housing portion 30" and which has a central boss-like extension 454 which fits into a recess provided in the end face of housing portion 30". Extension 454 defines an interior chamber 456 which is in fluid communication with the inner passage of housing portion 30" via an axial bore or passage 458. Pump 450 includes check valve means 460 comprising a valve element 462 within the inner passage of housing portion 30" and axially adjacent the armature piston portion 250". A valve seat element 464 is held between the end of ferrule extension 454 and housing portion 30" and is provided with a central opening 466 which is in registry with passage 458. A check valve spring 470 is located within chamber 456 of ferrule 452, one end of spring 470 contacting the inner wall surface of chamber 456 and the other end 474 of spring 470 being connected to valve element 462 by a link or connecting member 476, one end of which is connected to end 474 of spring 470 and the other end of which is secured to a central extension 478 on valve element 462.

Thus, check valve spring 470 is located external to the fluid chambers of pump 450. The rest volume resulting from locating the check valve spring 470 in the fluid chamber of pump 450 is thereby eliminated and the space available for spring 470 is large enough so that the desired spring rate is easily achieved. The arrangement of FIG. 5 maintains the feature of the basic configuration of the pump of FIGS. 1–3 by which the main check valve opens in response to a small pressure difference during the pump stroke but is held closed by a large spring force when at rest.

Valve seat element 464 is formed from flat sheet rubber and clamped between ferrule extension 454 and housing portion 30" for sealing. To this end extension 454 is provided with an annular extension 484 on the axial end thereof which locally compresses the rubber seat 464 for reliable sealing. Valve element 462 is of metal such as titanium and the clearance with the surface of the housing passage can be accurately controlled. Element 462 is provided with an annular skirt 490 on the one surface thereof to enhance sealing contact with seat element 464.

It may be desirable to adjust the armature plunger stroke after assembly of pump 450 by placing one or more shim elements between the end of the armature piston portion 250" and valve element 462. One such shim is designated 492 in FIG. 5 and is suitably mounted on the axial end face of piston portion 250". The small displacement pump 450 can be provided with a bypass orifice in a manner similar to either of the pumps 10 or 330 of FIGS. 1–3. For example, as shown in FIG. 5, passage 274" can be made small enough in diameter to serve as a bypass orifice in the manner previously described. In addition, pump 450 can be provided with an orifice in the path of fluid flow from the pump outlet in a manner similar to that of pump 10 in FIG. 1. In fact, pump 450 can include either or both of bypass or outlet orifices depending upon the requirements of the fluid system of which it is a part. Pump 450 operates in a manner similar to pump 10 and 330 in pumping fluid therethrough.

Figure 6:
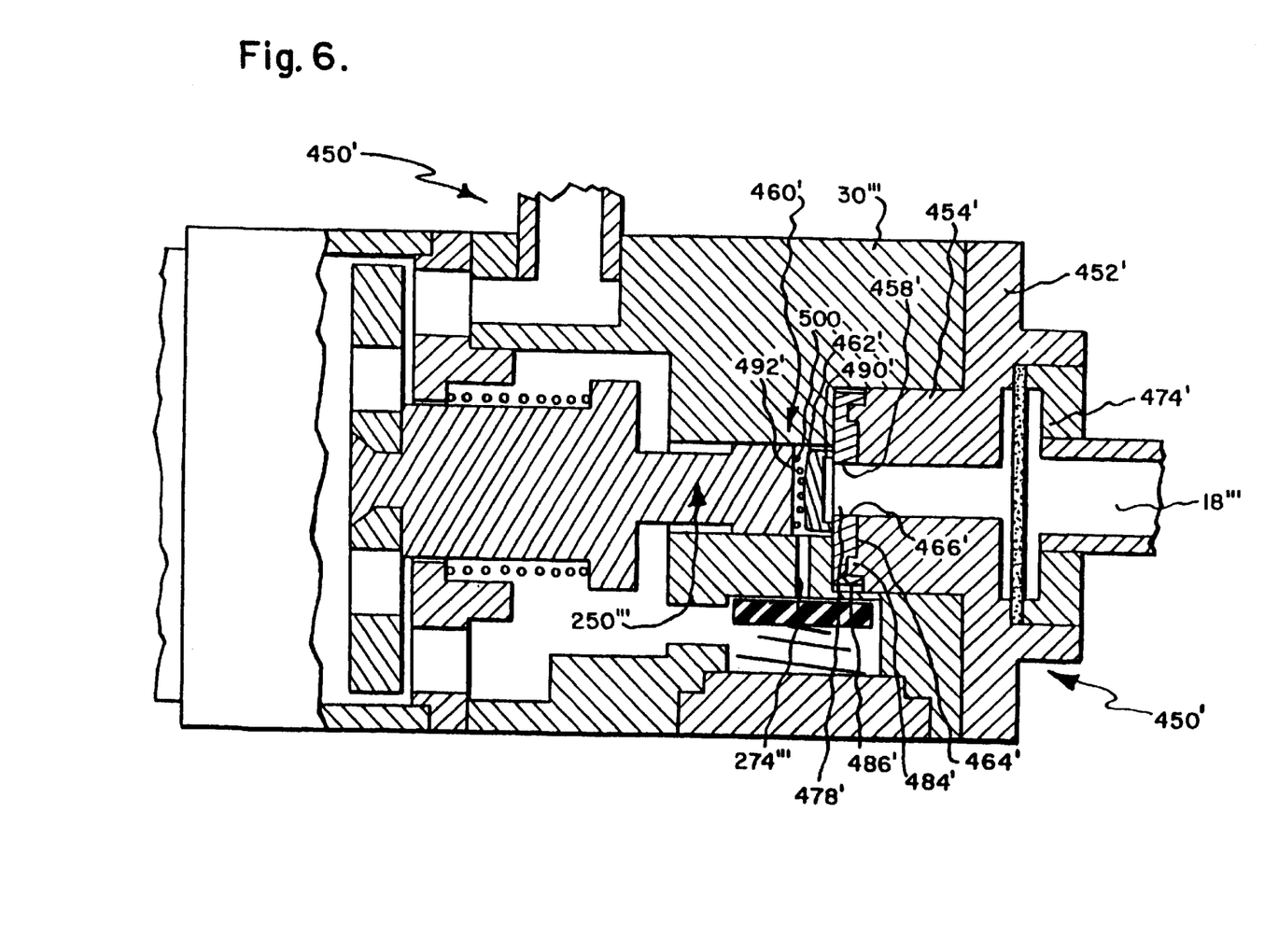
FIG. 6 is a fragmentary longitudinal sectional view of an alternative version of the pump of FIG. 5.

FIG. 6 shows an alternative version of the pump of FIG. 5. In FIG. 6 components similar to those of the pump of FIG. 5 are identified by the same reference numeral provided with a prime designation. Likewise, components similar to those of the pump of FIGS. 1–3 have the same reference numeral with a triple prime designation. In the configuration of FIG. 6 the main check valve is similar to that shown in FIG. 5 except that the conical check valve spring 500 is retained in its position between valve element 462 and the piston face. In this case the configuration offers no reduction in the rest volume of the pump chamber but it does increase the diameter of the check valve at the diameter at which it seals as compared to the configurations of FIGS. 1–3. It is believed that it will improve the dynamics of the flow during the early part of the pump stroke.

It is therefore apparent that the present invention accomplishes its intended objects. While embodiments of the present invention have been described in detail, that is for purpose of illustration, not limitation.

What is claimed is:

1. An electromagnetic pump comprising:
   a) a housing having an interior fluid containing region including a fluid receiving chamber and a fluid pumping chamber in fluid communication therewith, an inlet in fluid communication with said receiving chamber and an outlet in fluid communication with said pumping chamber;
   b) check valve means operatively associated with said fluid containing region for allowing fluid flow in a direction from said inlet through said outlet and blocking fluid flow in a direction from said outlet through said inlet;

c) electromagnet means carried by said housing and located external to said fluid containing region;

d) an armature positioned in said fluid containing region of said housing having a pole portion located for magnetic attraction by said electromagnet means and having a piston portion operatively associated with said fluid receiving and pumping chambers for forcing fluid from said receiving chamber through said outlet, said armature being movably supported in said housing for movement from a rest position through a forward pumping stroke when attracted by said electromagnet means to force fluid from said receiving chamber through said outlet and for movement in an opposite direction through a return stroke back to said rest position, said armature piston portion being located between a plunger portion and said pump inlet and movable within said housing, there being a relatively small clearance between said armature piston portion and said housing;

e) means defining a magnetic circuit including said electromagnet means and said armature and a gap between said pole portion of said armature and said electromagnet means for moving said armature toward said electromagnet means to close said gap in response to electrical energization of said electromagnetic means;

f) means extending from said outlet for providing a path for fluid flow from said pump; and g) means in said fluid flow path for providing an orifice in the path of fluid flow from said outlet so as to reduce the effect of the momentum of the fluid stream through the pump on the volume of fluid delivered during each pump cycle.

2. A pump according to claim 1, wherein said means for providing a fluid flow path from said pump comprises relatively rigid tubing connected at one end to said pump outlet and wherein said orifice providing means is located adjacent the other end of said tubing.

3. A pump according to claim 2, wherein said orifice providing means is at a location which insures that fluid pressure within the pump remains positive during deceleration of said piston during the forward pumping stroke.

4. A pump according to claim 1, wherein the pulse volume of the pump is from about 0.4 $\mu$L to about 0.6 $\mu$L and the diameter of said orifice is about 0.0055 inch.

5. An electromagnetic pump comprising:

a) a housing having an interior fluid containing region including a fluid receiving chamber and a fluid pumping chamber in fluid communication therewith, an inlet in fluid communication with said receiving chamber and an outlet with said pumping chamber;

b) check valve means operatively associated with said fluid containing region for allowing fluid flow in a direction from said inlet through said outlet and blocking fluid flow in a direction from said outlet through said inlet;

c) electromagnet means carried by said housing and located external to said fluid containing region;

d) an armature positioned in said fluid containing region of said housing having a pole portion located for magnetic attraction by said electromagnet means and having a piston portion operatively associated with said fluid receiving and pumping chambers for forcing fluid from said receiving chamber through said outlet, said armature being movably supported in said housing for movement from a rest position through a forward pumping stroke when attracted by said electromagnet means to force fluid from said receiving chamber through said outlet and for movement in an opposite direction through a return stroke back to said rest position, said armature piston portion being located between a plunger portion and said pump inlet and movable within said housing, there being a relatively small clearance between said armature piston portion and said housing;

e) means defining a magnetic circuit including said electromagnet means and said armature and a gap between said pole portion of said armature and said electromagnet means for moving said armature toward said electromagnet means to close said gap in response to electrical energization of said electromagnetic means;

f) catheter means for providing a path for fluid flow away from said pump;

g) accumulator means connected in fluid communication with one end of said catheter means; and h) means for placing said accumulator means in fluid communication with said outlet of said pump.

6. A pump according to claim 5, wherein said accumulator means has sufficient compliance to receive the entire volume of a single pump stroke with a pressure increase low enough so that operation of said pump is not disturbed.

7. A pump according to claim 5, wherein said accumulator means has compliance low enough so that moderate back pressure builds up within said accumulator means during a pump stroke.

8. A pump according to claim 5, wherein said catheter means is of a dimension such that the volume of a single pump stroke is completely discharged from said accumulator means between pump strokes.

9. A pump according to claim 5, wherein said accumulator means and said catheter means are dimensioned so as to be critically damped by viscous flow through said catheter means.

10. A pump according to claim 5, further including means for providing an outlet orifice between said pump outlet and said accumulator means.

11. A pump according to claim 5, further including:

a) controlled means for providing a bypass path for bubbles in the fluid around said armature piston portion between said fluid pumping chamber and said fluid receiving chamber only during said return stroke of said armature; and b) means in said bypass path for providing an orifice for fluid flow in the bypass path so as to decelerate the flow of fluid through the pump and limit the inertial flow volume in the pump.

* * * * *

UNITED STATES PATENT AND TRADEMARK OFFICE
CERTIFICATE OF CORRECTION

PATENT NO. : 6,193,477 B1 Page 1 of 1
APPLICATION NO. : 09/342372
DATED : February 27, 2001
INVENTOR(S) : Falk et al.

It is certified that error appears in the above-identified patent and that said Letters Patent is hereby corrected as shown below:

Title Page; item (60)

Under Related U.S. Application Data (last line):

"August 11, 1994" should read -- March 11, 1994 --

Signed and Sealed this

Seventeenth Day of July, 2007

JON W. DUDAS
*Director of the United States Patent and Trademark Office*